United States Patent

Kopelowicz

[11] Patent Number: 5,816,249
[45] Date of Patent: Oct. 6, 1998

[54] LATEX PROPHYLACTICS ADHERED TO A DEFORMED KNITTED FABRIC AND THEIR MANUFACTURING PROCEDURE

[76] Inventor: Alberto Kopelowicz, Calle 103 No. 1155/61, 1650 San Martin Buenos Aires, Argentina

[21] Appl. No.: 683,796

[22] Filed: Jul. 18, 1996

[30] Foreign Application Priority Data

Apr. 30, 1996 [AR] Argentina ................... 336351
Jul. 16, 1996 [AR] Argentina ................... 337489

[51] Int. Cl.⁶ ........................................ A61F 6/02
[52] U.S. Cl. ......................... 128/842; 128/844; 128/918
[58] Field of Search ................... 128/842, 844, 128/918; 604/347–353

[56] References Cited

U.S. PATENT DOCUMENTS 2,586,674  2/1952  Lönne ........................... 128/844
4,881,553  11/1989 Grossman ...................... 604/347
5,109,871  5/1992  Thornton ....................... 128/844
5,513,652  5/1996  Schwartz ....................... 128/844

*Primary Examiner*—Michael A. Brown
*Attorney, Agent, or Firm*—Kuhn and Muller

[57] ABSTRACT

A procedure for the manufacturing of an improved condom features a knitted fabric adhered to the condom. The fabric is deformed in a longitudinal sense in relation to its axle, by means of a system through which the fabric, in the shape of a tube, is introduced into a cone. Two parallel conveyor bands with fastening devices are adhered to the fabric. Once the fabric is cut through in the middle of both bands, it is conveniently guided onto the condom matrixes where elastomeric rings deform and fit it tight. The whole set thus obtained is ready to be dipped into an adhesive coating and later dried after which drying, electrically heated metallic rings cut away the remainder of the fabric that failed to adhere to the condom. Thus the latter is rolled and readied for packaging.

3 Claims, 9 Drawing Sheets

LATEX PROPHYLACTICS ADHERED TO A DEFORMED KNITTED FABRIC AND THEIR MANUFACTURING PROCEDURE

FIELD OF THE INVENTION

The present invention refers to a prophylactic having a knitted fabric adhered to it from its closed end. The fabric is deformed in a longitudinal sense in relation to its axis. This makes the condom highly resistant and reliable, featuring great practical advantages. The manufacturing procedure for the prophylactic of the present invention is also detailed below.

BACKGROUND OF THE INVENTION

Condoms made out of latex or other in-kind elastomeric material are known in the market, all of which have been notoriously and definitely improved by the subject matter of the present invention. It consists of the introduction, during the condom's manufacturing stage, of a layer of knitted is fabric, deformed in a longitudinal sense in relation to the condom's axis, which is preferably capable of avoiding longitudinal stretching and permitting transversal elasticity, thus decreasing almost to zero the chances of tearing.

OBJECTS AND SUMMARY OF THE INVENTION

Although it is true that it seems apparently easy to introduce this knitted fabric, practice has proven that complex means must be dealt with to obtain the best results in the procedure for the present invention of the improved product referred to above. It is necessary to develop the following procedure, detailed below, consisting basically in the manufacturing of a machine that bears a rectangular structure at which vertexes, by means of axles and bearings, pinions revolve and in turn move a flapped chain that carries supports, at which ends there are hubs within which axles slide. The axles have the condom matrixes attached to one of their ends and at the other end they bear sliding devices which act on cams. It should be emphasized that the knitted fabric in the shape of a tube is introduced into a cone, where two parallel conveyor bands having fastening devices adhere to the fabric. Once the fabric is cut through the middle of both conveyor bands it is guided and placed over the condom matrixes. The axles where the condom matrixes are attached to slide downwards, introducing themselves into the elastomeric rings which are located in compartments fixed to a chain, which is parallel, and cooperates with the previously mentioned flapped chain. The elastomeric rings fix the fabric tight to the prophylactic. The fabric is cut at a line above the elastomeric ring to allow the condom matrix, upon sliding upwards, to take along the whole set including the prophylactic, the deformed fastened fabric, and the elastomeric ring, and thus free itself from the ring carrier chain. The set is then dipped into an adhesive coating and later placed in an oven for drying. The left over portion of unused fabric is then cut away and the elastomeric ring withdrawn. The prophylactic is then withdrawn from the condom matrix to be tested as usual, rolled up, siliconed and packaged.

DETAILED DESCRIPTION OF THE DRAWINGS

It is noted that FIGS. 1–5 show the preferred embodiment of the present invention. Moreover, FIGS. 6–10 show an alternate embodiment for providing a prophylactic in accordance with the present invention.

Figures 1, 1A:
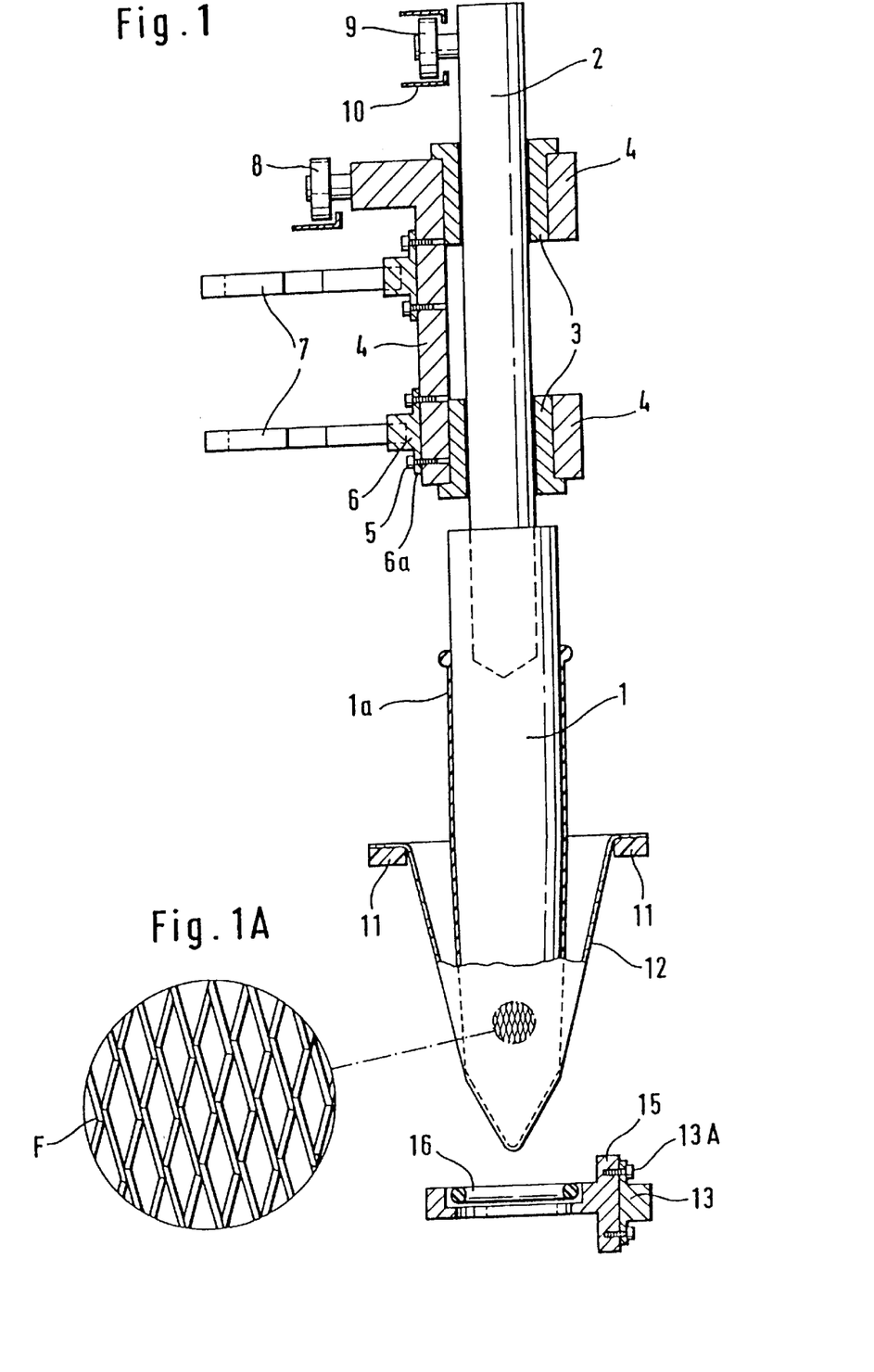
FIG. 1 is a side elevational view of a prophylactic condom being formed in accordance with the present invention.
FIG. 1A is a close up view of the weave of the prophylactic condom as in FIG. 1.

FIG. 1 is a side view showing the condom matrix (1). Reference numeral (1a) shows the prophylactic placed over the condom matrix. Reference numeral (2) shows the axle where the condom matrix is attached to, and reference numeral (3) shows the hubs within which the axle (2) slides. Reference numeral (4) shows carrier set for the hubs (3), which is fastened, through screws (5), to the chain (6) by means of flaps (6a). Pinions (7) move the chain (6). Wheel (8) holds the carrier set (4) in a horizontal position. Reference numeral (9) shows the wheel resting on the cams (10) thus allowing the axle (2) to slide. Reference numeral (11) shows the two conveyor bands having an adhering surface to which the fabric (12) becomes fixed. Reference numeral (13) shows the flapped carrier chain which, by means of screws (13a), is fastened to the set (15) which in turn carries an elastomeric ring (16).

FIG. 1A shows the fabric (F) deformed in a longitudinal sense in relation to the axle of the condom matrix.

Figure 2:
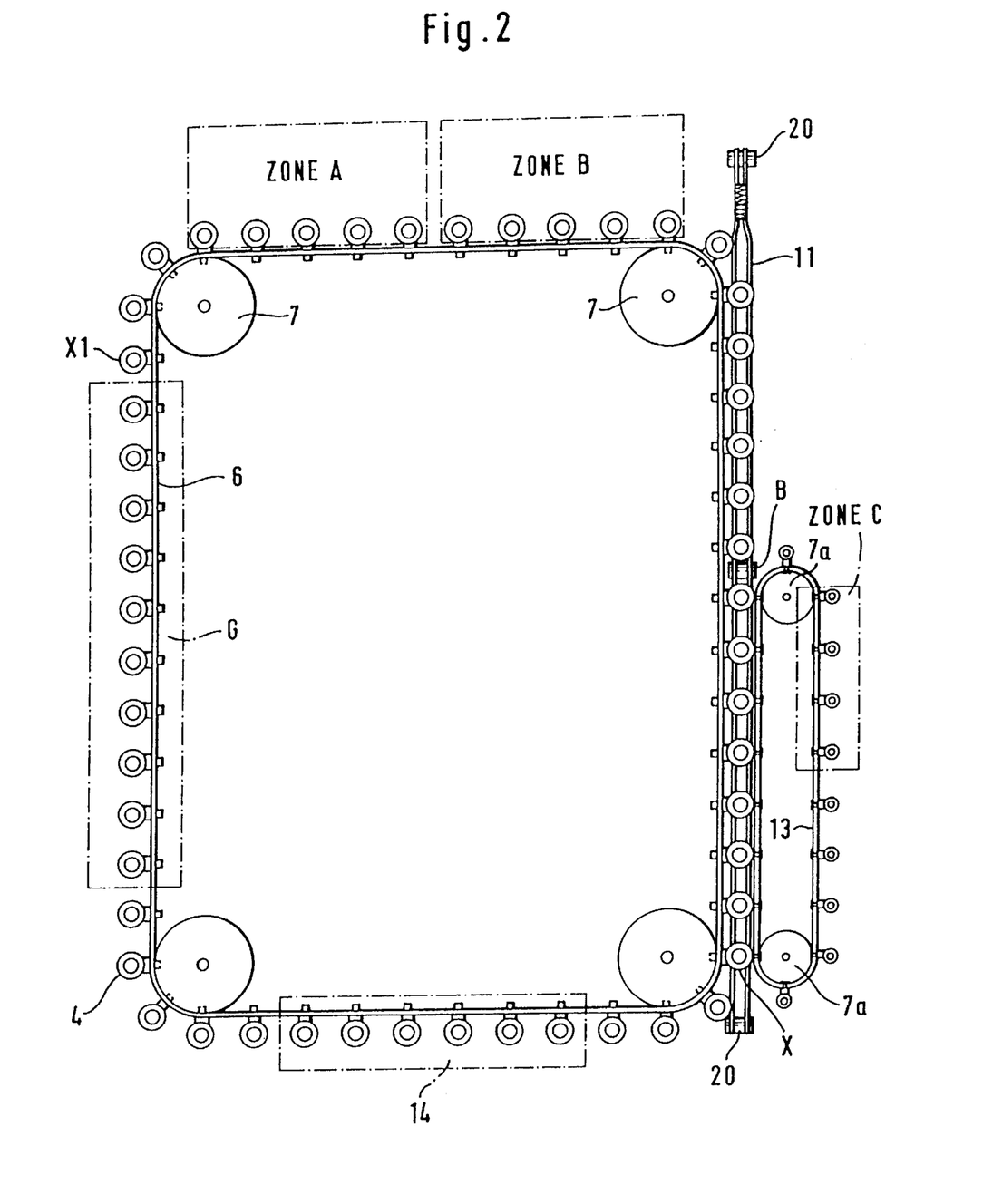
FIG. 2 is a plan view of an apparatus forming a plurality of prophylactic condoms, such as the condom in FIG. 1.

FIG. 2 is a plan view showing the chain (6) carrying the carrier sets (4), where the condom matrixes with their corresponding hubs, axles, cams and wheels are found. Reference character (C) shows the pinions that move the chain (6). Chain (13) bears the elastomeric ring carrier sets. Reference numeral (14) represents the adhesive coating. Reference character (G) shows the oven used for drying. Reference character (X) shows the first cutting device used to separate the unused remains of the fabric that covers the prophylactic, which is placed on the corresponding condom matrix. Another cutting device (X1) performs the cutting of fabric one millimeter above the adhesion line in order to dispose of the greatest possible amount of fabric not adhered to the condom. Pinions (7a) move the chain (13). Roller (B) regulates the height of the conveyor bands (11). Rollers (20) move the bands (11). Zone "A" shows where the elastomeric ring as well as the finished condom are withdrawn. Zone "B" shows where the prophylactic is placed on the condom matrix. Zone "C" shows the place where the elastomeric rings (16) are once again placed within the set (15).

Figures 3, 3A, 3B:
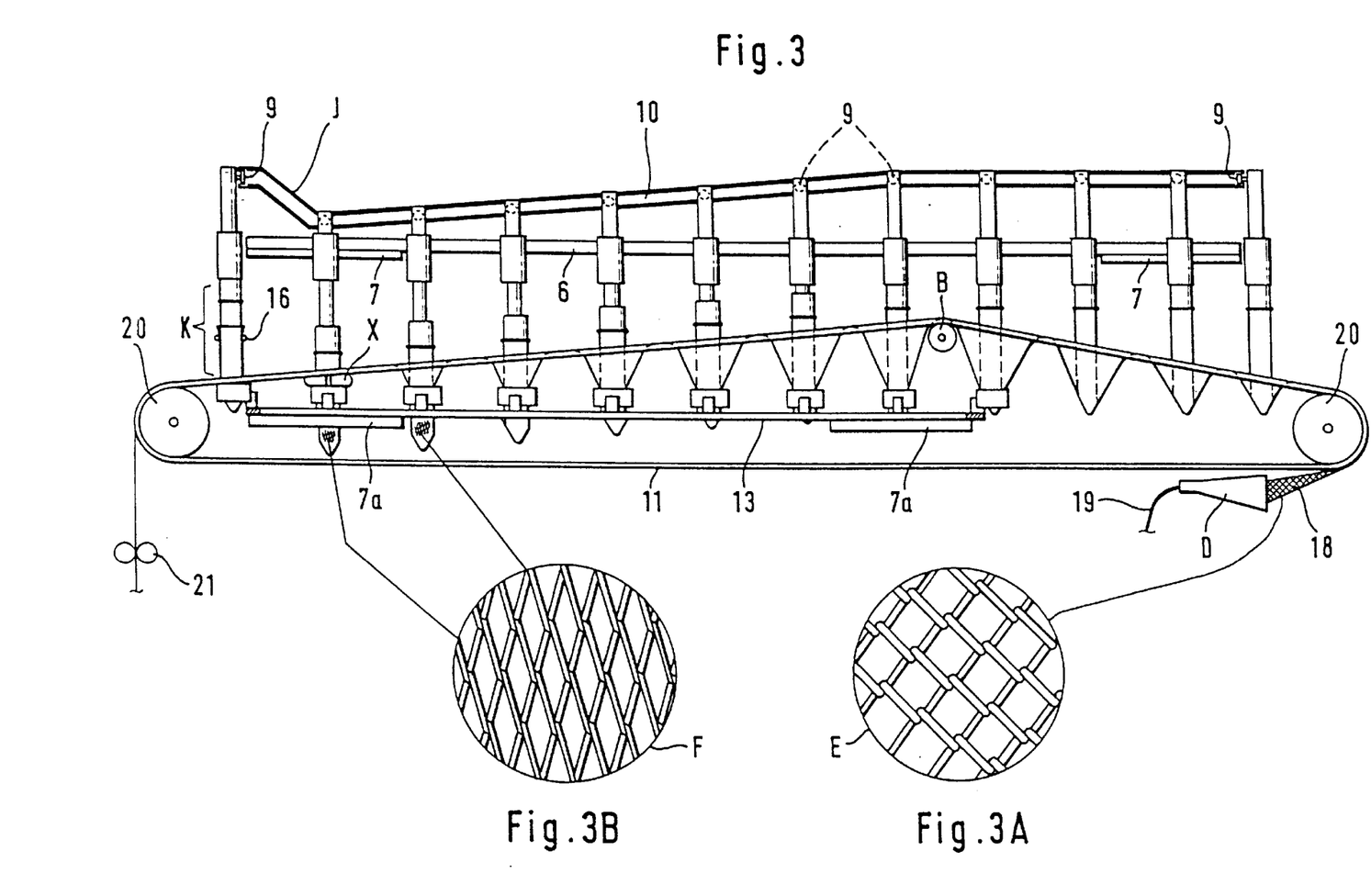
FIG. 3 is a side view of the apparatus for forming a plurality of prophylactic condoms as in FIG. 2.
FIG. 3A is a close up view of the weave of a fabric used in making the condom as in FIG. 1, before the prophylactic fabric is longitudinally stretched in accordance with the present invention.
FIG. 3B is a close up view of the weave of a fabric used in making the prophylactic condom as in FIG. 1, after the fabric is longitudinally stretched in accordance with the present invention.

FIG. 3 is a side view showing the fabric (19) as it enters into the cone (D). The fabric (19) adheres to the conveyor bands (11), and is then cut along the middle of both bands (18). Rollers (20) move the conveyor bands (11), which bands (11) in turn carry the fabric (19) towards a convenient position on the condom matrixes, as can be appreciated by the drawing. Roller (B) is used to regulate the conveyor bands (11) so that the knitted fabric can hold on tight, deform itself and rest on the prophylactic. Chain (13) holds the elastomeric ring carriers (7). Pinions (7a) move the chain (13). Wheels (9) act on the cam (10) so that the prophylactic, which is placed on the condom matrix and covered by the knitted fabric, may slide downwards to introduce itself into the elastomeric ring thus keeping the fabric (19) fastened to the condom. Reference numeral (16) shows the elastomeric ring at its best point in fastening the fabric (19). Reference character (K) shows the complete illustration of the condom matrix, the fabric (19) and the elastomeric ring, which matrix slides upwards taking along the elastomeric ring (16) and detaches itself from the chain and from the device that contains the elastomeric rings. Reference character (J) shows how the cam (10) moves upwards so that the wheel (9) can perform this operation. First cutting device (X) is used to separate the remaining portion of the unused fabric and thus is able to separate the whole set from the conveyor bands (11). Two rollers (21) are used to withdraw the unused remains, adhered to the conveyor bands (11).

As is shown in FIGS. 3A and 3B reference character (E) shows the fabric in its natural state as it enters into the cone (D) and reference character (F) shows the deformed fabric already placed over the prophylactic.

Figures 4, 4A:
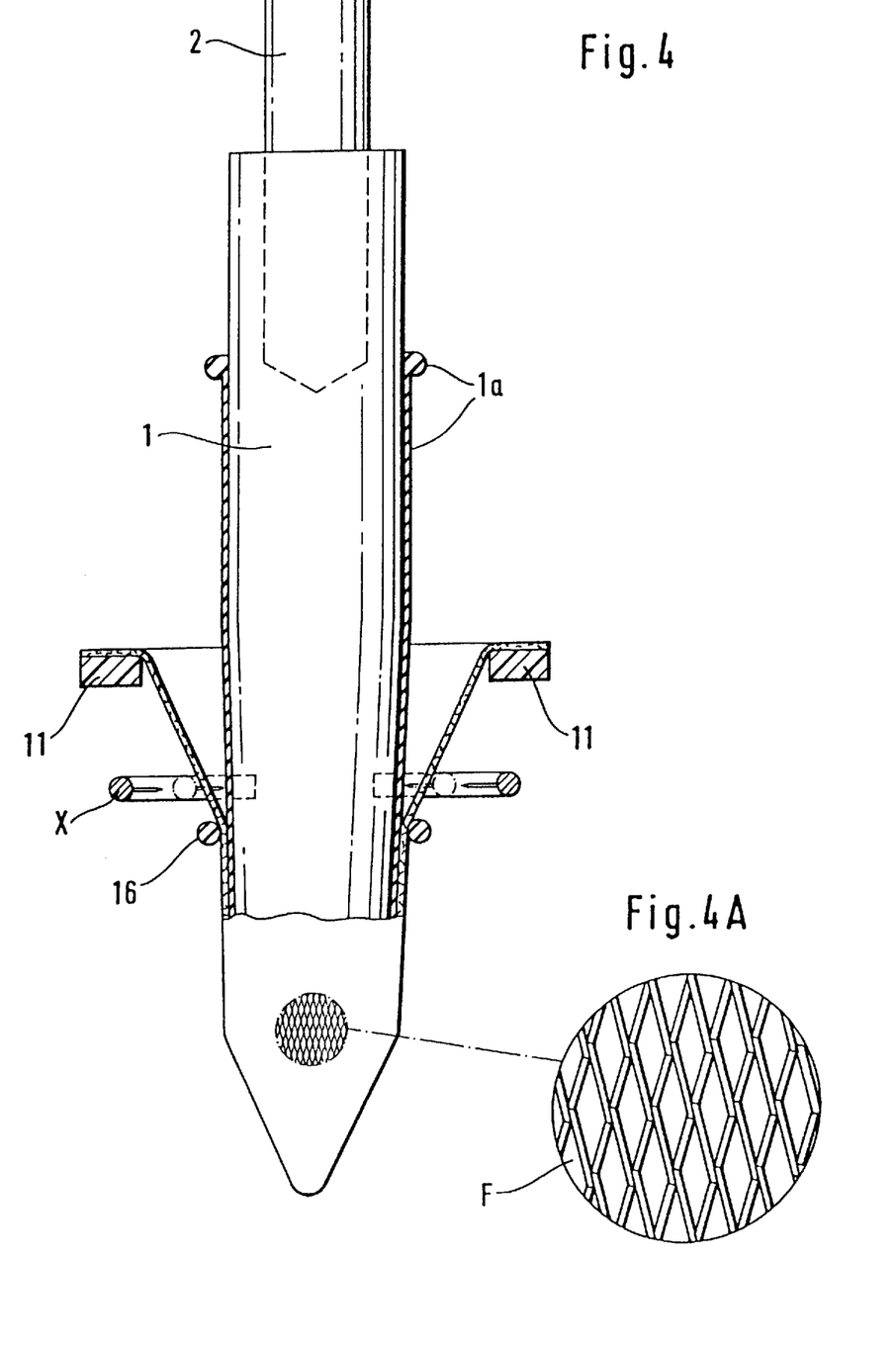
FIG. 4 is a side elevational view of the prophylactic condom made in accordance with the present invention.
FIG. 4A is a close up view of the weave of a fabric used in making the prophylactic condom as in FIG. 4, after the fabric is longitudinally stretched in accordance with the present invention.

FIG. 4 is a side view showing the condom matrix (1), the axle (2), the elastomeric ring (16), the parallel conveyor bands (11) which adhere to the fabric, the first cutting zone (X), and the deformed fabric (F) placed over the condom. Reference numeral (1a) shows the prophylactic placed on the condom matrix.

Figure 5:
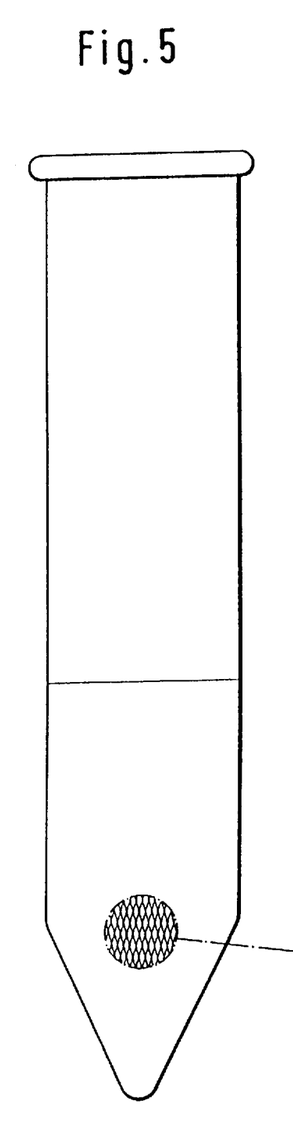
FIG. 5 is a side elevational view of the prophylactic condom of the present invention, shown with fabric adhered thereto.
Figure 5A:
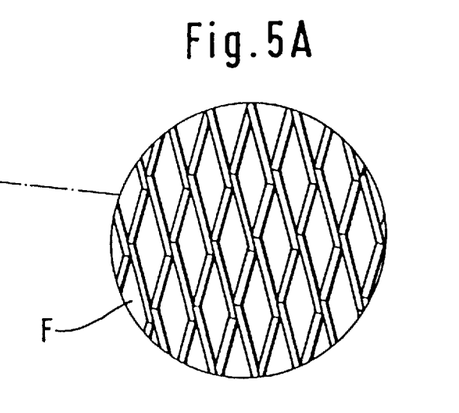
FIG. 5A is a close up view of the weave of the prophylactic condom as in FIG. 5.

FIG. 5 is a side view of the prophylactic already bearing the adhered fabric. Reference character (F) shows an enlarged view of the deformed fabric.

While FIGS. 1–5 show the preferred embodiment, FIGS. 6–10 show an alternate embodiment for forming the prophylactic of the present invention.

Figure 6:
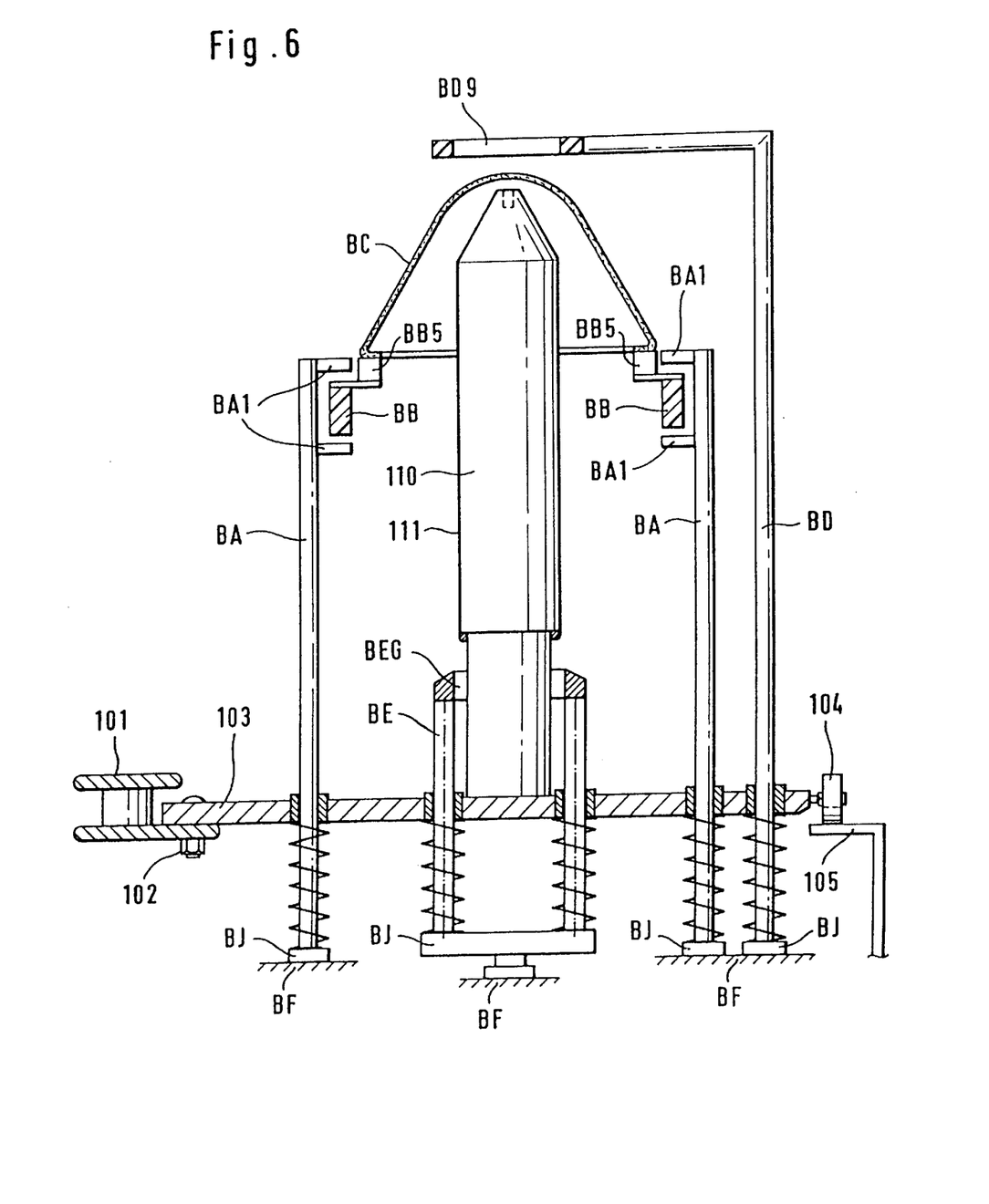
FIG. 6 is a side elevational view of an alternate embodiment for an apparatus for making a prophylactic condom in accordance with the present invention.

For example, FIG. 6 is a side view depicting a flapped chain (101) which is fixed to a carrier plate (103) by means of a screw (102). At the other end of the plate (103) there is a wheel (104) that rests on a support (105) to maintain horizontal stability. The axles are marked with letter (BA), which slide on the plate (103) where points (BA1) are present to hold tight and guide the conveyor bands (BB) that at point (BB5) have fastening devices, such as VELCRO®-type to hold the fabric. At reference character (BC) there is shown the fabric adhered to point B5. Reference character (BD) shows the axles sliding on the plate (103) and at one of its ends there lies an elastomeric ring (BD9) used to deform and fit the fabric tight (BC) to the matrix (110), which is covered by the condom (111). There is also shown the axles (EE) that slide on the plate (103) bearing, at one of its ends, a ring in the shape of a blade (BEG) which is electrically heated and is appropriate for cutting, by means of heat temperature, the remainder of the fabric that did not adhere to the condom. Letter (BJ) shows all the support points of the sliding axles that work in their own cams (BF).

Figure 7:
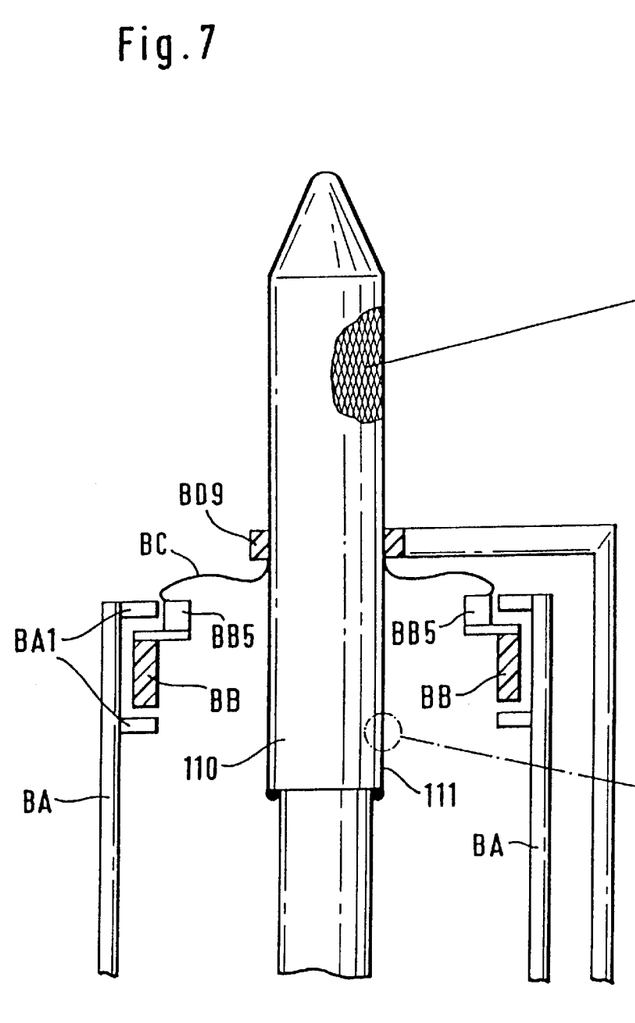
FIG. 7 is a side view of the prophylactic condom being formed in accordance with the alternate embodiment as in FIG. 6.
Figure 7A:
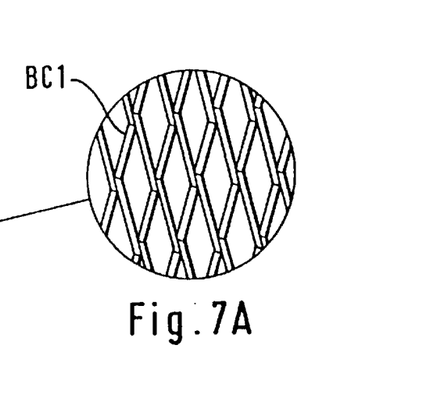
FIG. 7A is a close up view of the weave of the fabric of the prophylactic condom as in FIG. 6.
Figure 7B:
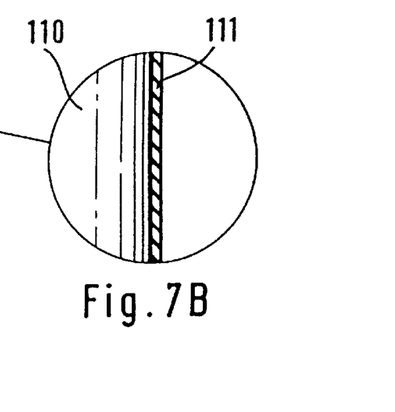
FIG. 7B is a close up side sectional view of the prophylactic condom as in FIG. 6.

FIG. 7 is a side view showing that once the rods (BA) have slid over to the base of the condom matrix (110), carrying the conveyor band (BB) that has the fabric (BC) fastened to it at point (BB5), it is made easier for the elastomeric ring (BD9) to deform and fit the fabric tight in a longitudinal sense in relation to the condom's axle (111). In frame (BC1) there is shown the fabric thus deformed.

Figure 8:
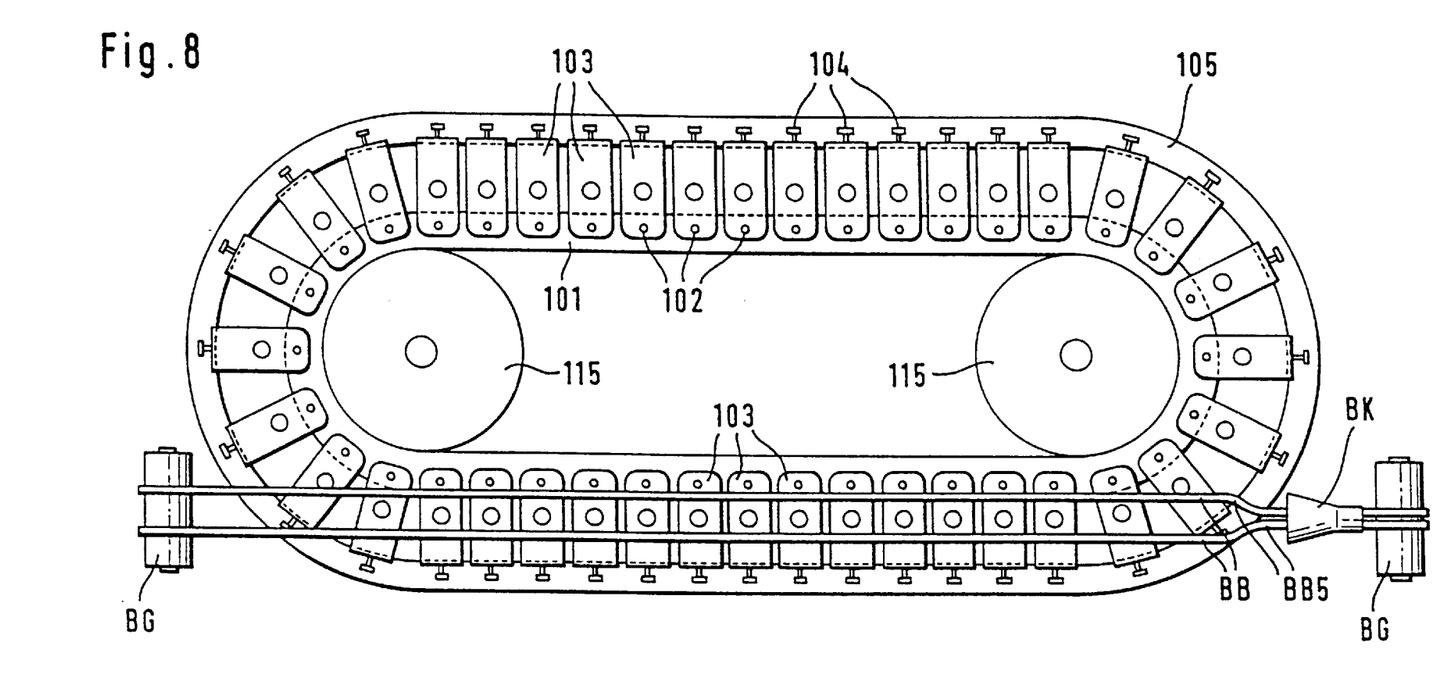
FIG. 8 is a top plan view of the alternate embodiment for the apparatus for making a prophylactic condom as in FIG. 6.

FIG. 8 is a plan view that shows the flapped chain (101) which, by means of screws (102) fixes a plate (103) at which end the wheel (104) acts upon the track (105). These features are all moved by pinions (115) located at both ends. FIG. 8 also shows two conveyor bands (BB) that rotate by means of the pulleys (BG) and rest on the cone (BK) to adhere to the fabric through a fastening system (BB5).

Figure 9:
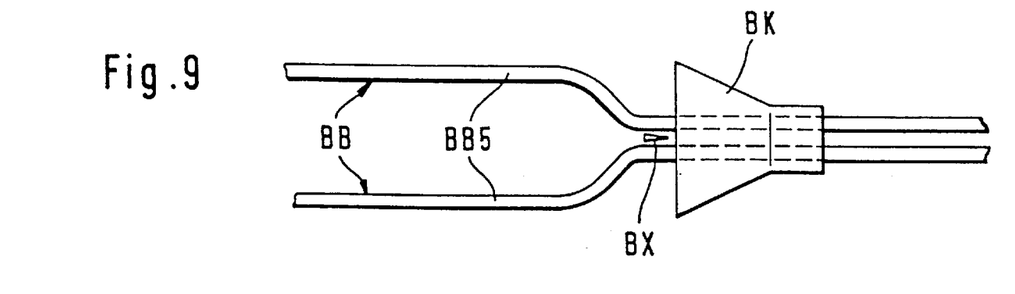
FIG. 9 is a top plan view of the cone portion of the apparatus as in FIGS. 6 & 8.

FIG. 9 is a plan view of the cone (BK) where the fabric in the shape of a tube is externally introduced. Two parallel conveyor bands (BB) that have fastening devices (BB5) are adhered to the fabric. In the middle of both bands there is provided a cutting device (BX) which works immediately after the fabric is adhered by the mentioned devices (B5). FIG. 9 also shows how the conveyor bands (BB) come apart to adequately locate themselves on the matrixes.

Figure 10:
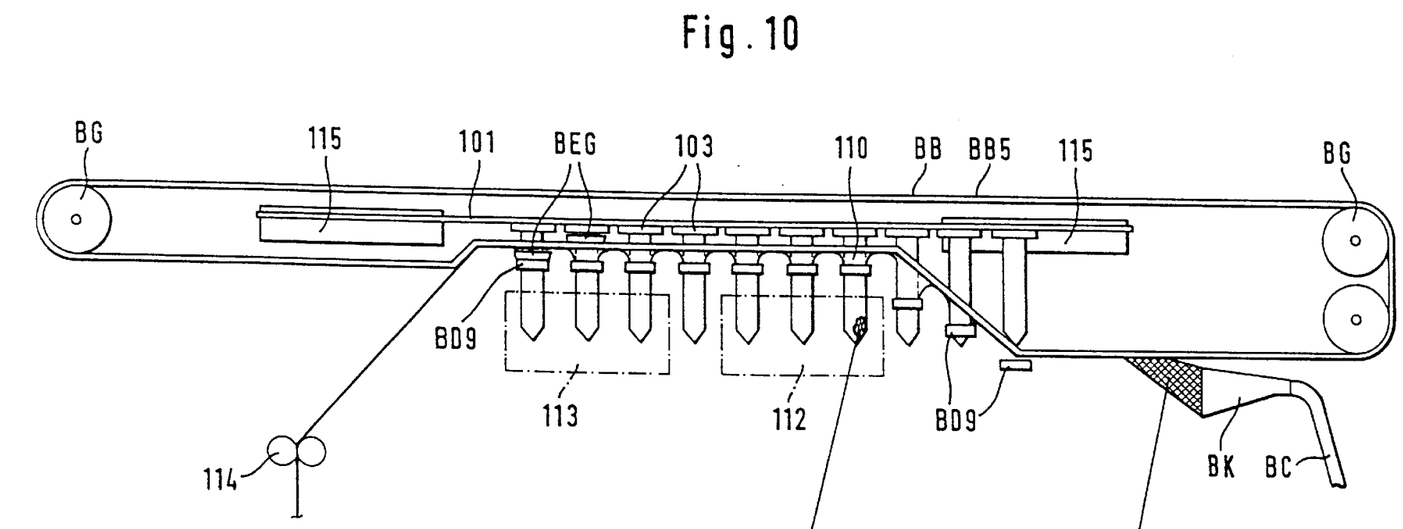
FIG. 10 is a side view of the apparatus as in FIGS. 6, 8 and 9.

FIG. 10 is a side view in which is shown the chain (101) moved by the pinions (115) that carry the condom matrixes (110) upon which the elastomeric rings (BD9), as well as the cutting blades (BEG), act. Fabric (BC) is shown being introduced into the cone (BK). FIG. 10 also shows the conveyor bands (BB) that, through their devices (BB5), adhere to the fabric, which after being cut, is conveniently located on the condom matrixes (110). Once the rings (BD9) do their job, the prophylactic is all introduced into the adhesive coat (112) and later dried in the oven (113). That part of the fabric which has not become adhered to the condom is separated from it by means of cylinders shaped as blades (BEG), after which the cylinders (114) take away the remaining portion of fabric from the machine's circuit.

Figures 10A, 10B:
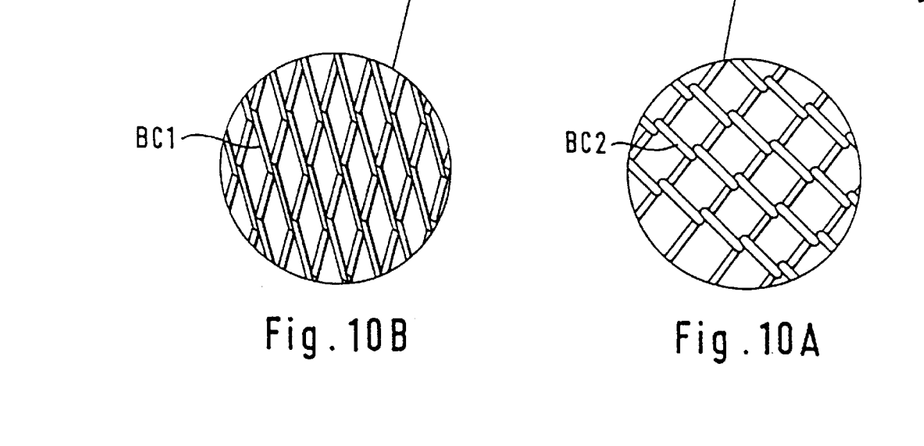
FIG. 10A is a close up view of the weave of the fabric as in the alternate embodiment for the condom as in FIG. 6, before longitudinal stretching of the fabric.
FIG. 10B is a close up view of the weave of the fabric as in the alternate embodiment for the condom as in FIG. 6, after longitudinal stretching of the fabric.

FIG. 10A shows the fabric (BC2) as it is introduced into the cone (BK) in its natural state. In FIG. 10B, the fabric (BC1) is shown deformed and fitted tightly to the condom by the elastomeric ring (BD9).

Other modifications may be made to the present invention, without departing from the scope of the invention, as noted in the appended claims.

I claim:

1. An improved prophylactic comprising a prophylactic tube including the adhesion of a knitted fabric starting from a closed end of said prophylactic, said fabric being previously deformed to make said fabric inelastic in a longitudinal sense in relation to a longitudinal axis of said prophylactic axis.

2. A procedure for the manufacturing of a prophylactic according to claim 1, comprising the steps by which a knitted fabric in the shape of a tube is introduced into a cone and two parallel conveyor bands that have fastening devices adhere to said fabric; said fabric, after being cut in the middle of both bands, is adequately guided onto said prophylactics, which said prophylactics are in turn placed on the condom matrixes where elastomeric rings deform and fasten the fabric tight; wherein further the whole set is ready to be dipped into an adhesive coating and later dried, after which some electrically heated devices cut away any left over fabric that did not adhere to said prophylactic, and said prophylactic is subsequently rolled up and readied for packaging.

3. An improved prophylactic comprising a prophylactic having a knitted fabric adhered to said prophylactic from the closed end of said prophylactic, said fabric being previously deformed to make it inelastic in its longitudinal sense in relation to an axis of said prophylactic.

\* \* \* \* \*